(12) United States Patent
Ramjit et al.

(10) Patent No.: US 12,220,490 B2
(45) Date of Patent: Feb. 11, 2025

(54) ADHESIVE PATCH CONTAINING AN IMPROVED RELEASE LINER SYSTEM

(71) Applicant: EUROMED, INC., Orangeburg, NY (US)

(72) Inventors: Ravi Ramjit, Dix Hills, NY (US);
Michael Talian, Northvale, NJ (US);
Semyon Itskovich, Fair Lawn, NJ (US)

(73) Assignee: EUROMED, INC., Orangeburg, NY (US)

( * ) Notice: Subject to any disclaimer, the term of this patent is extended or adjusted under 35 U.S.C. 154(b) by 1180 days.

(21) Appl. No.: 16/474,866

(22) PCT Filed: Dec. 29, 2017

(86) PCT No.: PCT/US2017/069007
§ 371 (c)(1),
(2) Date: Jun. 28, 2019

(87) PCT Pub. No.: WO2018/126170
PCT Pub. Date: Jul. 5, 2018

(65) Prior Publication Data
US 2019/0350873 A1    Nov. 21, 2019

Related U.S. Application Data

(60) Provisional application No. 62/440,966, filed on Dec. 30, 2016.

(51) Int. Cl.
*A61K 9/70* (2006.01)
*A61F 13/00* (2024.01)
(Continued)

(52) U.S. Cl.
CPC ...... *A61K 9/7046* (2013.01); *A61F 13/00063* (2013.01); *A61F 13/00076* (2013.01); *A61F 13/00085* (2013.01); *A61F 13/0259* (2013.01); *A61K 9/703* (2013.01); *A61K 9/7038* (2013.01); *A61K 9/7053* (2013.01); *A61K 9/7061* (2013.01); *A61K 9/7069* (2013.01); *A61P 17/10* (2018.01); *B32B 37/12* (2013.01); *B32B 38/10* (2013.01); *C09J 7/21* (2018.01);
(Continued)

(58) Field of Classification Search
None
See application file for complete search history.

(56) References Cited

U.S. PATENT DOCUMENTS

| | | |
|---|---|---|
| 5,998,694 A | 12/1999 | Jensen et al. |
| 6,495,158 B1 | 12/2002 | Buseman et al. |

(Continued)

FOREIGN PATENT DOCUMENTS

| | | |
|---|---|---|
| CN | 1756539 A | 4/2006 |
| CN | 101111209 A | 1/2008 |

(Continued)

OTHER PUBLICATIONS

Machine translation of JP 2014511851 A (Year: 2014).*
International Search Report dated Mar. 13, 2018, in PCT/US2017/069007 (7 pages).

*Primary Examiner* — Frank D Ducheneaux
(74) *Attorney, Agent, or Firm* — Farber LLC

(57) ABSTRACT

An adhesive patch is described that contains an improved release liner for the treatment of various skin conditions.

18 Claims, 5 Drawing Sheets

(51) Int. Cl.
*A61F 13/02* (2006.01)
*A61P 17/10* (2006.01)
*B32B 37/12* (2006.01)
*B32B 38/10* (2006.01)
*C09J 7/21* (2018.01)
*C09J 7/22* (2018.01)
*C09J 7/30* (2018.01)
*C09J 7/40* (2018.01)
*C09J 109/06* (2006.01)
*C09J 125/10* (2006.01)

(52) U.S. Cl.
CPC . *C09J 7/22* (2018.01); *C09J 7/30* (2018.01); *C09J 7/40* (2018.01); *C09J 109/06* (2013.01); *C09J 125/10* (2013.01); *A61F 2013/00582* (2013.01); *A61F 2013/00812* (2013.01); *C09J 2301/408* (2020.08)

(56) References Cited

U.S. PATENT DOCUMENTS

| | | |
|---|---|---|
| 9,078,948 B2 | 7/2015 | Jensen et al. |
| 2001/0019722 A1 | 9/2001 | Fotinos et al. |
| 2011/0105977 A1 | 5/2011 | Hart |
| 2013/0152944 A1 | 6/2013 | Okada et al. |
| 2015/0157509 A1 | 6/2015 | Atkinson et al. |

FOREIGN PATENT DOCUMENTS

| | | | |
|---|---|---|---|
| CN | 101180019 A | | 5/2008 |
| CN | 201558223 U | | 8/2010 |
| CN | 101883560 A | | 11/2010 |
| CN | 102625677 A | | 8/2012 |
| CN | 102755216 A | | 10/2012 |
| CN | 103596529 A | | 2/2014 |
| CN | 104622641 A | | 5/2015 |
| CN | 106176131 A | | 12/2016 |
| EP | 0750892 A2 | | 1/1997 |
| EP | 2078517 A2 | | 7/2009 |
| EP | 2517680 A2 | | 10/2012 |
| JP | 09-501909 A | | 2/1997 |
| JP | 2004511851 A | * | 5/2014 |
| KR | 10-2000-0022054 A | | 4/2000 |
| KR | 10-0987287 B1 | | 10/2010 |
| KR | 10-1232543 B1 | | 2/2013 |
| WO | 9500122 A1 | | 1/1995 |
| WO | 2007065428 A1 | | 6/2007 |

* cited by examiner

ADHESIVE PATCH CONTAINING AN IMPROVED RELEASE LINER SYSTEM

CROSS-REFERENCE TO RELATED APPLICATIONS

This application is the § 371 national stage entry of International Application No. PCT/US2017/069007, filed on Dec. 29, 2017, which claims priority to U.S. Provisional Application No. 62/440,966, filed on Dec. 30, 2016.

TECHNICAL FIELD

The present invention relates to an adhesive patch containing an improved release liner system for the treatment of various skin conditions. The improved release liner system permits rapid application of the adhesive patch to the skin with minimal risk of damage to the patch in the process and also minimizes applicator contact during application of the patch.

BACKGROUND

Adhesive dressings or patches are used for covering and treating different skin conditions, such as scratches, wounds, insect bites, acne, eczema, herpes and warts, and may serve to simultaneously camouflage irregularities while treating the skin condition.

In addition, selected adhesive dressings or patches (such as those containing hydrogels or hydrocolloids) promote a moist environment and may themselves facilitate healing of the skin condition being addressed. This healing effect may be further enhanced by the presence of various active ingredients.

There is a constant need for improved ease and reproducibility in the application of adhesive dressings or patches to a targeted skin area in view of the often sensitive nature of the skin area and the optimized therapeutic benefits achieved with proper placement of the dressing or patch. The present invention addresses this need through the presence of an improved release liner system that results in the rapid and consistently accurate positioning of adhesive dressings or patches to a targeted skin area with minimal problems. The improved release system is particularly effective when incorporated into small, thin skin patches that have previously lacked a release system which allows for minimal finger touching of the adhesive by the applicator during the application process and also lacked a way to prevent the small adhesive patch from folding or bending onto itself.

SUMMARY OF THE INVENTION

An aspect of the present invention is a flexible adhesive patch arrangement comprising: (i) a flexible adhesive patch comprising: a backing having two sides; and a therapeutic adhesive composition coated on at least a portion of one side of the backing, where the therapeutic adhesive composition is capable of adhering to mammalian skin; and (ii) a liner completely covering the adhesive composition, where the liner contains a means for readily separating the liner into two portions, with each portion being in contact with the adhesive composition.

In an exemplary embodiment, the means for separating is a perforated pattern or a slit that partially or completely penetrates the liner.

In an exemplary embodiment, the two portions of the liner are different in size.

In an exemplary embodiment, the two portions of the liner are substantially similar in size.

In an exemplary embodiment, the area of the liner is larger than the area of the adhesive composition. In various particular embodiments, the adhesive composition covers 10 to 100% of the surface area of the liner, such as 20 to 100%, such as 25 to 100%, such as 30 to 100%, such as 35 to 100%, such as 40 to 100%, such as 45 to 100%, such as 50 to 100%, such as 60 to 100%, such as 70 to 100%, such as 80 to 100%, such as 90 to 100%.

In an exemplary embodiment, the liner comprises one or more of a polyester film, a polyolefin film, siliconized paper and a plastic laminated paper.

In an exemplary embodiment, the liner has a thickness of about 0.01 to about 0.5 mm, such as 0.01 to 0.4 mm, such as about 0.01 to 0.3 mm, such as 0.05 to 0.5 mm, such as 0.05 to 0.3 mm.

In an exemplary embodiment, the backing is porous and/or permeable. In another embodiment, the backing is occlusive. In a particular embodiment, the occlusive backing achieves a moisture vapor transmission rate (MVTR)<100 $g/m^2/24$ h. In another embodiment, the backing is waterproof and breathable and achieves a MVTR>500 $g/m^2/24$ h.

In an exemplary embodiment, the backing has a thickness of about 0.02 to about 1.0 mm, such as about 0.04 to about 1.0 mm, such as about 0.05 to about 1.0 mm, such as about 0.02 to about 0.8 mm, such as about 0.02 to about 0.5 mm, such as about 0.05 to about 0.3 mm.

In an exemplary embodiment, the backing comprises polycellulose fibers, polyester fibers, polyurethane fibers, polyolefin fibers, polyamide fibers, cotton fibers, copolyester fibers, or any mixture thereof. In another exemplary embodiment, the backing comprises polycellulose film, polyurethane film, polyester film, polyethylene film, polyolefin film or any mixture thereof.

In an exemplary embodiment, the therapeutic adhesive composition is a pressure adhesive composition and may comprise one or more of a polyacrylamide, xanthum gum, guar gum, a hydrocolloid, a starch, a vinyl acetate copolymer, polyvinyl pyrrolidone, polyvinyl alcohol, polyethylene oxide, a polyacrylate, polymaleic acid, polymaleic anhydride, a polyurethane, a polyurea, maltodextrin, carboxymethyl cellulose and carboxypropyl cellulose.

In an exemplary embodiment, the therapeutic adhesive composition comprises one or more of a hydrogel, a polyurethane gel, a hydrocolloid, an acrylic, a rubber and a silicone gel.

Exemplary hydrocolloids include, but are not limited to, alginic acid and salts thereof, chitin, chitosan, pectin, cellulose and cellulose derivatives (such as cellulose ethers or cellulose esters), linked or cross-linked carboxyalkylcellulose or hydroxyalkylcellulose, polyvinyl alcohol, polyvinyl pyrrolidone, agar and gelatin.

Other exemplary hydrocolloids include, but are not limited to, polyacrylates or their salts may further be used as a hydrocolloid where the polyacrylate may be present as a homopolymer, copolymer or block polymer.

In an exemplary embodiment, the therapeutic adhesive composition has a thickness of about 0.01 to about 1.5 mm, such as about 0.03 to about 1.2 mm, such as about 0.05 to about 1.0 mm, such as about 0.1 to about 1.0 mm, such as about 0.3 to about 1.0 mm, such as about 0.5 to about 1.0 mm.

In an exemplary embodiment, the therapeutic adhesive composition comprises a topical acne agent, a wart-removing agent, a cold sore agent, an agent for treating psoriasis, an agent for treating dermatitis (such as atopic dermatitis (eczema), seborrheic dermatitis, contact dermatitis, allergic contact dermatitis (ACD), irritant contact dermatitis (ICD)) a free radical scavenger, a moisturizing agent, a wrinkle reduction agent or any combination thereof.

In an exemplary embodiment, the topical acne agent is selected from the group consisting of salicylic acid, resorcinol, benzoyl peroxide, sulfur, retinol, retinal, retinoic acid, an alpha hydroxy acid, vitamin C, vitamin A, hyaluronic acid, vegetable oils, coconut oil, jojoba oil, avocado oil, olive oil, hemp oil, peptides, corticosteroids, pharmaceutically acceptable salts of any of the preceding, and any combination thereof.

In an exemplary embodiment, the topical acne agent is present in an amount of about 0.05 to about 10 wt. %, such as 0.1 to 10 wt %, such as 0.5 to 10 wt %, such as 1.0 to 10 wt %, such as 0.05 to 5 wt %, such as 0.1 to 5 wt %, such as 0.5 to 5 wt %, such as 1.0 to 5 wt %, of the therapeutic adhesive composition.

In an exemplary embodiment, the therapeutic adhesive composition further comprises water, an alcohol or a combination thereof.

In an exemplary embodiment, the alcohol is glycerol, bisabolol, polyethylene glycol propylene glycol, ethylene glycol or mixtures thereof.

In an exemplary embodiment, the therapeutic formulation comprises a skin conditioner.

In an exemplary embodiment, the therapeutic formulation comprises an antimicrobial agent.

In an exemplary embodiment, the therapeutic formulation comprises an antiseptic agent.

In an exemplary embodiment, the therapeutic adhesive composition is thicker at the center than at the edges. In a particular embodiment, the thickness of the edge is 0.10 to 0.80, such as 0.2 to 0.7, such as 0.1 to 0.5, such as 0.3 to 0.5, of the thickness of the center.

In an exemplary embodiment, the backing and the therapeutic adhesive composition have a circular or triangular or rectangular or square or oval shape or the like.

In an exemplary embodiment, the liner and the adhesive patch are different in color.

In an exemplary embodiment, the adhesive patch arrangement is enclosed in a sealed package.

In an exemplary embodiment, the arrangement is enclosed in a sealed paper or poly/plastic packaging material, or combination thereof.

In an exemplary embodiment, the adhesive and the packaging materials are sterilizable or sterilized.

In an exemplary embodiment, the backing has a diameter of 0.1 to 5 inches, such as 0.5 to 5 inches, such as 1 to 5 inches, such as 2 to 5 inches, such as 0.1 to 3 inches, such as 0.1 to 2 inches, such as 0.2 to 1 inch, such as 0.2 to 0.5 inches.

Another aspect of the present invention is a method for attaching the adhesive patch described herein to a targeted skin area of a mammal in need thereof, the method comprising: detaching one of the two liner portions from the adhesive patch arrangement to expose a first portion of the adhesive composition of the adhesive patch; attaching the exposed first portion of the adhesive composition to the targeted skin area; detaching the second of the two liner portions from the adhesive patch arrangement to expose the remaining portion of the adhesive composition of the adhesive patch while the exposed first portion of the adhesive composition remains attached to the targeted skin area; and attaching the exposed remaining portion of the adhesive composition to complete attachment of the adhesive patch to the targeted skin area.

In an exemplary embodiment, the mammal is a human.

In an exemplary embodiment, the targeted skin area is the face, neck, shoulder, chest, back, elbow, inner elbow or any combination thereof.

In an exemplary embodiment, the adhesive patch is attached to the targeted skin area for a period of about 10 minutes to about 72 hours, such as about 30 minutes to about 72 hours, such as about 1 to about 72 hours, such as about 6 to about 72 hours, such as about 12 to about 72 hours, such as about 24 to 72 hours, such as about 1 to about 48 hours, such as about 6 to about 48 hours, such as about 12 to about 48 hours, such as about 24 to 48 hours, such as about 1 to about 24 hours, such as about 3 to about 24 hours, such as about 6 to about 24 hours, such as about 12 to 24 hours.

In an exemplary embodiment, the means for separating is a perforated pattern or a slit that partially or completely penetrates the liner.

Another aspect of the present invention is a method for treating or preventing a disorder or condition of the skin of a mammal in need thereof, comprising applying to the affected skin surface an adhesive patch as described herein for an period of time effective to treat or prevent the skin disorder or condition.

In an exemplary embodiment, the disorder or condition is selected from the group consisting of acne, warts, *Herpes labialis* (cold sores), atopic dermatitis, seborrheic dermatitis, contact dermatitis, allergic contact eczema, psoriasis, shingles, hives, insect bites, age spots (lentigo or solar lentigines) and wrinkles.

In an exemplary embodiment, the disorder is (*Acne vulgaris*) acne.

Another aspect of the present invention is a sheet composed of multiple copies of the adhesive patch arrangement as described herein arranged in parallel, wherein the slit or the perforated pattern present in each copy forms a single uninterrupted line that extends the length or width of the sheet.

In an exemplary embodiment, each copy is separated from an adjacent copy by a different readily separable perforated pattern or slit.

In an exemplary embodiment, each different perforated pattern or slit cumulatively forms a single uninterrupted line that extends the length or width of the sheet.

BRIEF DESCRIPTION OF THE DRAWINGS

The following drawings illustrate specific embodiments of the present invention and are not intended to otherwise narrow the scope of the invention as described herein.

DETAILED DESCRIPTION

Backing Layer

Figure 1:
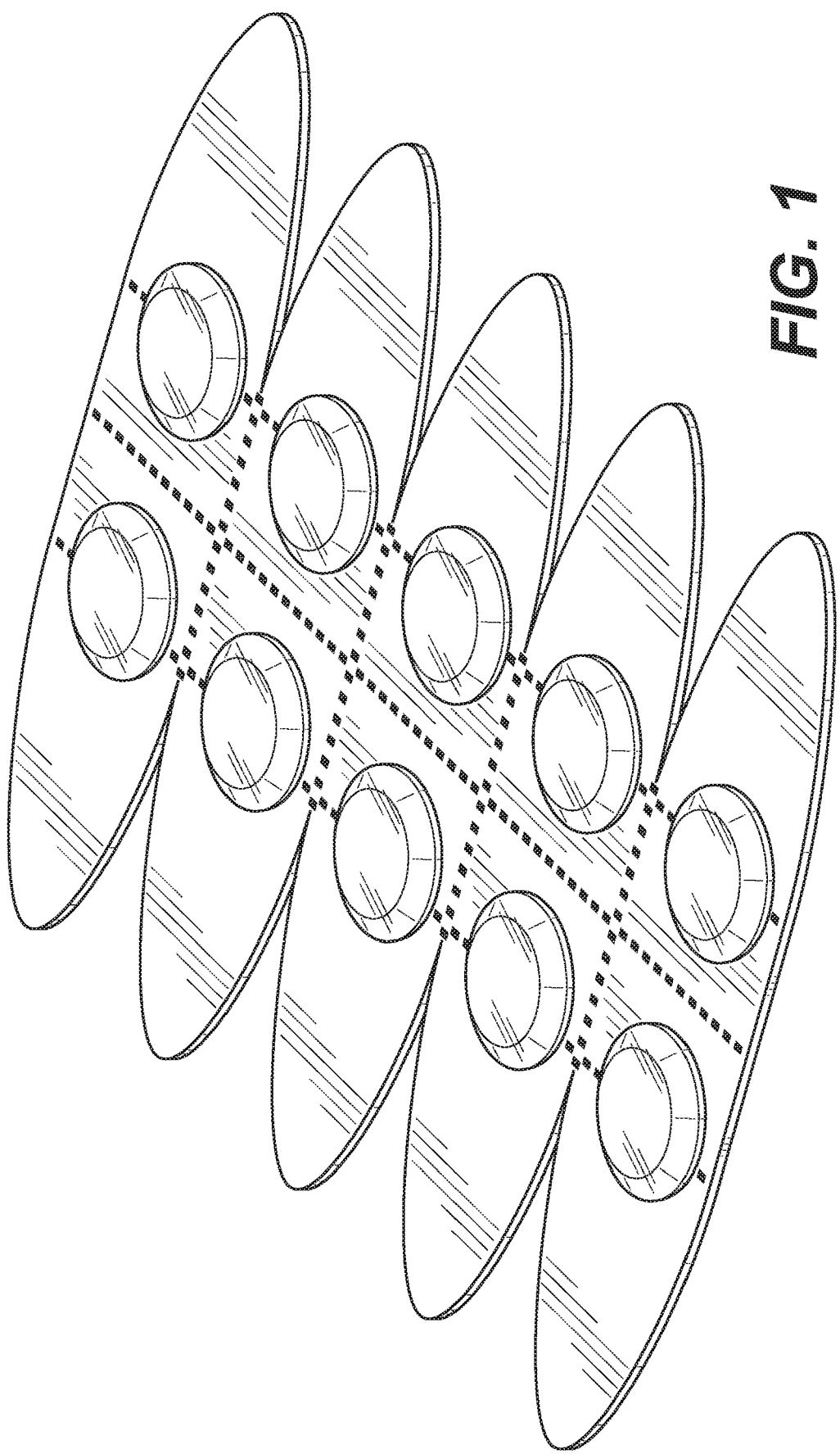
FIG. 1 shows a top view of a particular packaging array of 10 circular adhesive patches, where the single longitudinal (lengthwise) perforation line and the four latitudinal (widthwise) perforation lines allow for separation of the array into 10 individual adhesive patches. The single perforation line that runs under each of the adhesive patches allows for the step-wise removal of the release liner from the therapeutic adhesive layer of the patch, which represents an improved process for applying the patch to the skin that is an aspect of the present invention.
Figure 2:
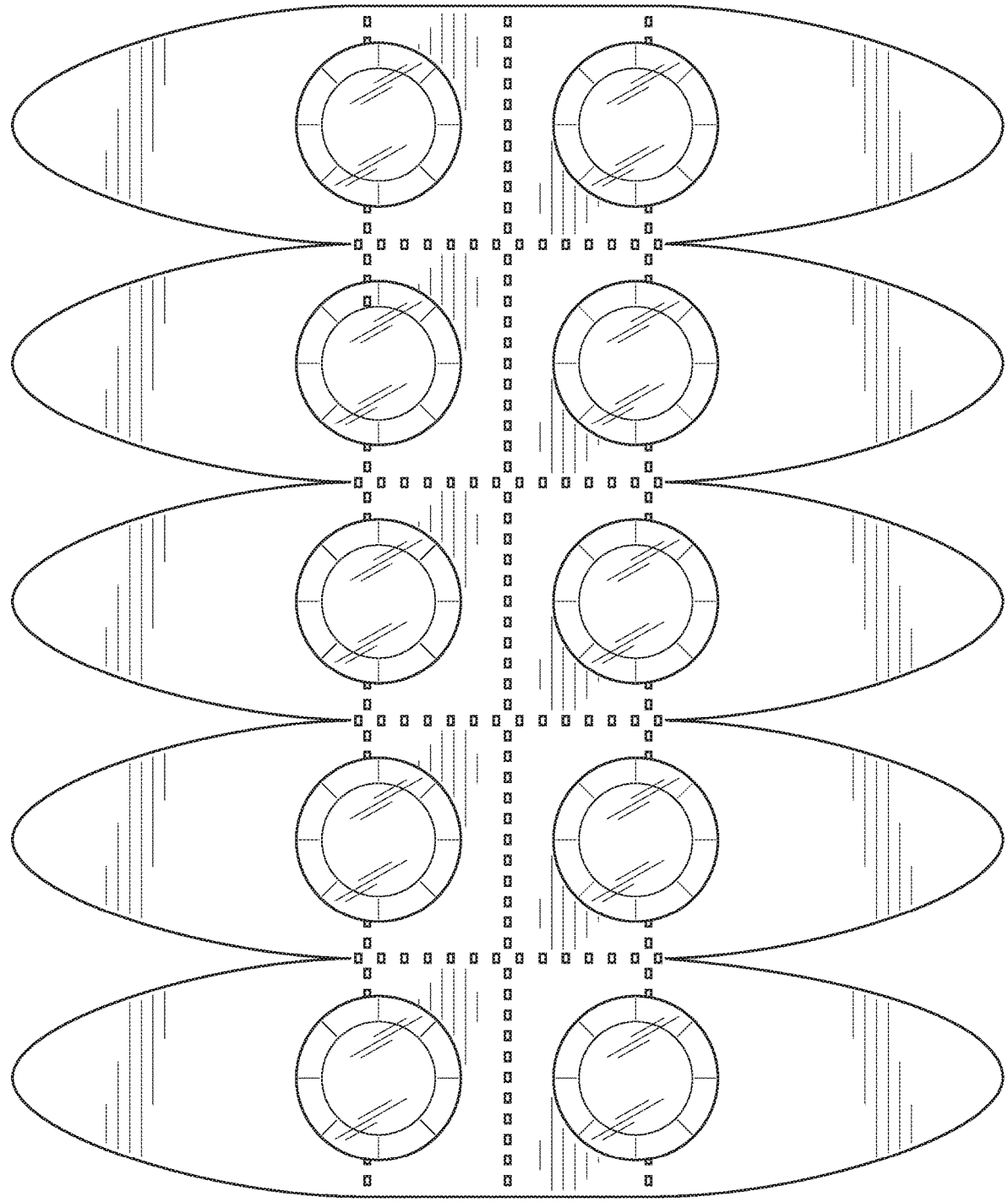
FIG. 2 is a top view of the array of FIG. 1 that clearly shows the perforation lines necessary for separation of an individual patch from the array of 10 and the single perforation line positioned under each patch that allows for the step-wise removal of the release liner from the therapeutic adhesive layer of the patch.
Figure 3:
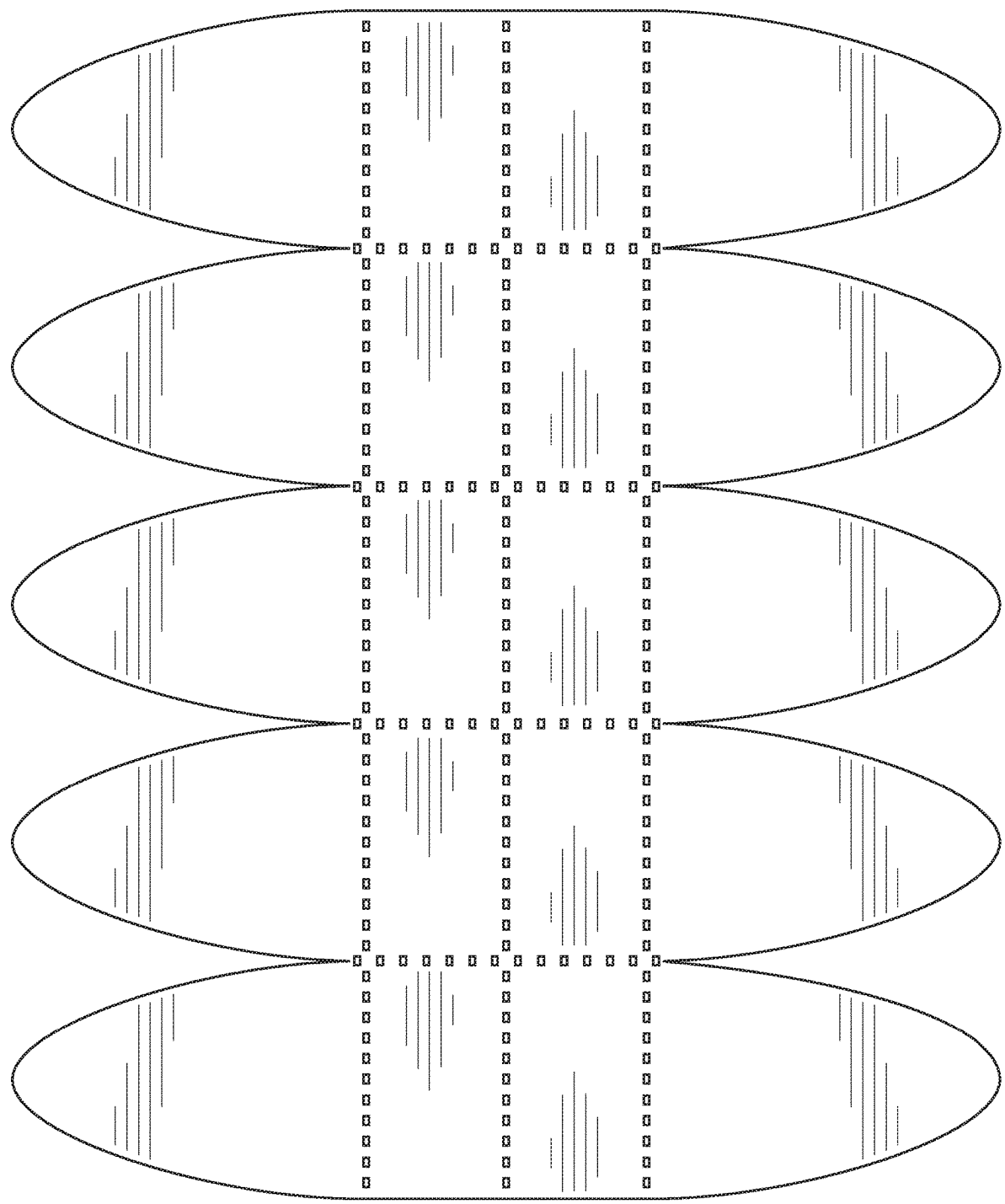
FIG. 3 is the back view of the array of FIG. 1 that shows the release liner and the perforation lines.
Figure 4:
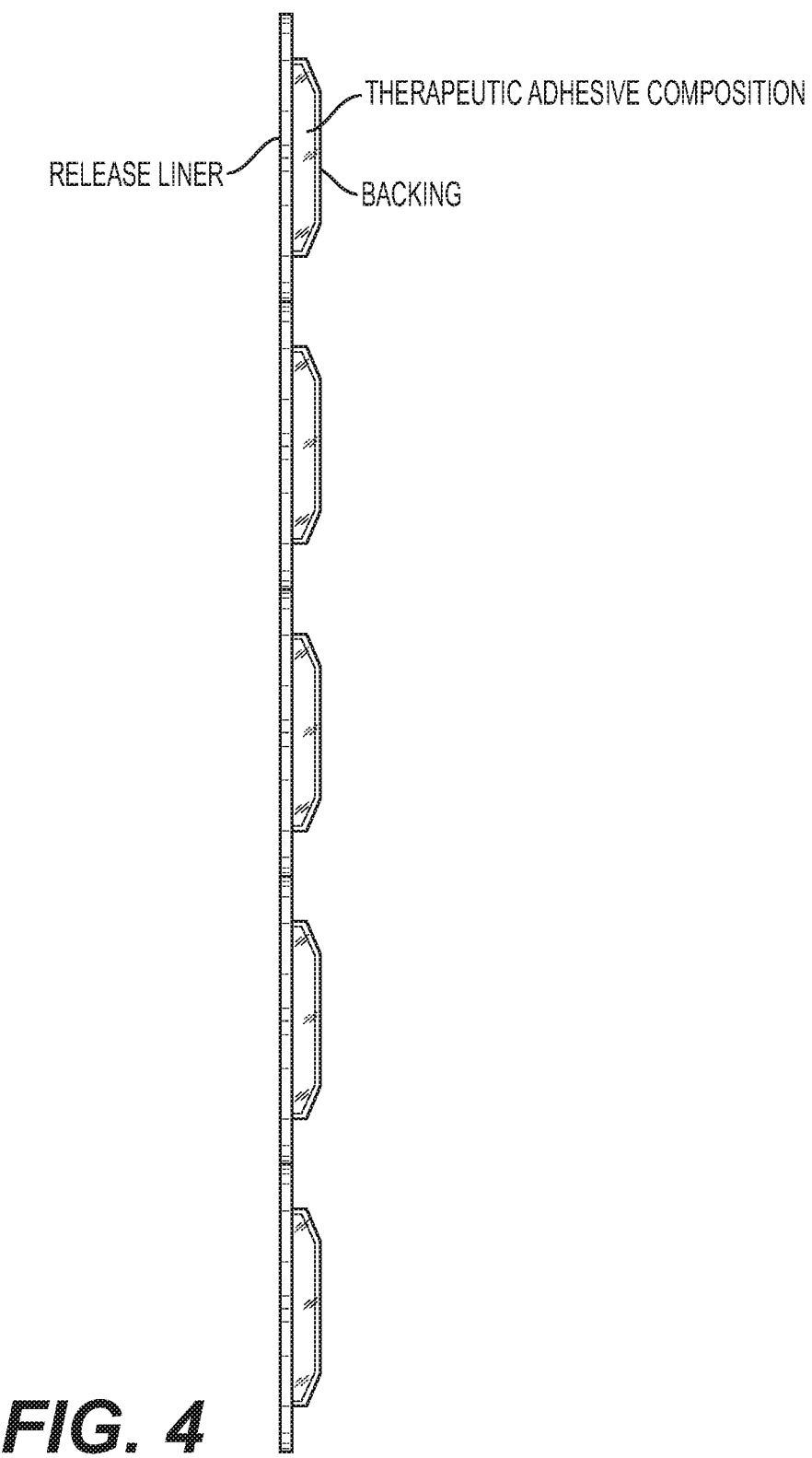
FIG. 4 is a side view of a particular packaging array of the adhesive patches that identifies the backing and the therapeutic adhesive composition components of each patch and the release liner in contact with the therapeutic adhesive composition layer.
Figure 5:
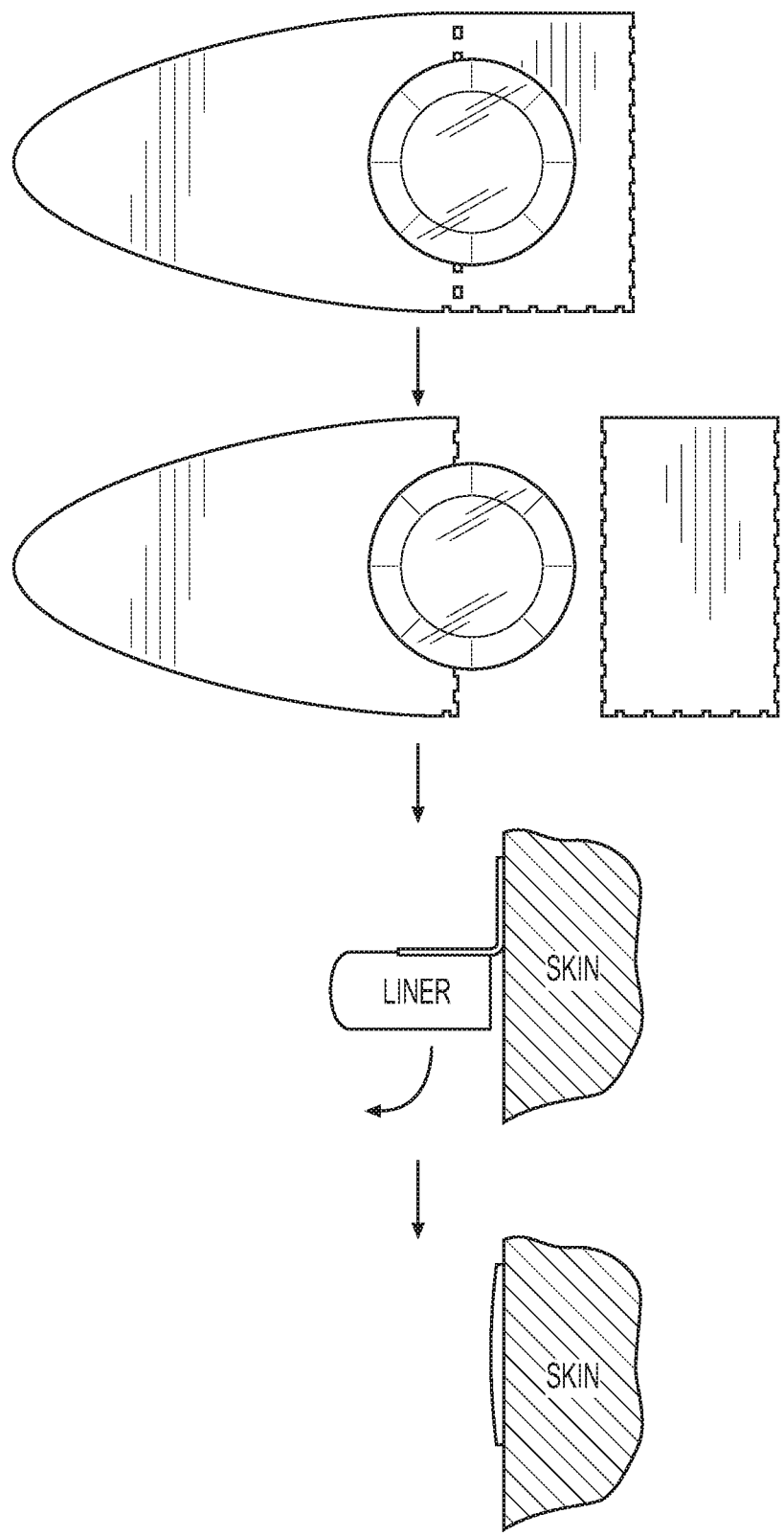
FIG. 5 depicts a two-step process for applying the adhesive patch that promotes accurate positioning of the patch to a targeted skin area with minimal fingering of the therapeutic adhesive layer and minimal risk of undesired folding or bending of the patch onto itself.

The backing layer comprises may comprise any suitable material known for use in the preparation of wound dressings and includes, but is not limited to, a foam, a polyurethane, a polyethylene, a polyester, a polyamide, polycellulose, cotton, or any mixture thereof. In an exemplary embodiment, the backing is flexible, pliable, and/or stretchable. In an exemplary embodiment, the backing contains two sides, a front side and a back side. In an exemplary embodiment, the backing layer is vapor or moisture permeable and able to achieve a MVTR>300 g/m$^2$/24 h, but is liquid impermeable. In an exemplary embodiment, the backing layer is continuous (e.g., no holes, perforations or indentations) or is discontinuous (e.g., containing holes, perforations or indentations). In an exemplary embodiment, the backing contains a hydrophobic sizing agent.

The backing layer has a suitable thickness for the intended use. In an exemplary embodiment, the backing layer has a thickness of 0.02 to about 1.0 mm, such as 0.03 to about 0.8 mm, such as about 0.05 to about 0.6 mm, such as about 0.07 to about 0.5 mm, such as about 0.1 to about 0.5 mm.

Therapeutic Adhesive Composition

The therapeutic adhesive composition of the present invention comprises or consists of any skin-friendly adhesive composition known for use in medical articles which contact mammalian (e.g., human) skin. Exemplary adhesive compositions may suitably be, but are not limited to, the types disclosed in U.S. 2013/0152944; 2011/0105977; U.S. Pat. Nos. 6,495,158; and 9,078,948.

In an exemplary embodiment, the therapeutic adhesive composition is a pressure sensitive therapeutic adhesive composition and may comprise one or more of a polyacrylamide, xanthum gum, guar gum, a hydrocolloid, a starch, a vinyl acetate copolymer, polyvinyl pyrrolidone, polyvinyl alcohol, polyethylene oxide, a polyacrylate, polymaleic acid, polymaleic anhydride, a polyurethane, a polyurea, maltodextrin, carboxymethyl cellulose, polyisobutylene, rubber, polybutene, carboxypropyl cellulose, polydimethylsiloxane, polystyrene-polybutadiene-polystyrene, polystyrene-polyisoprene-polystyrene, polystyrene-poly(ethylene-butylene)-polystyrene block polymers or any combination thereof.

In an exemplary embodiment, the therapeutic adhesive composition comprises a topical acne agent, such as but not limited to, salicylic acid, resorcinol, resorcinol acetate, benzoyl peroxide, sulfur, retinol, retinal, retinoic acid, an alpha hydroxy acid, vitamin C, vitamin A, hyaluronic acid, vegetable oils, coconut oil, jojoba oil, avocado oil, olive oil, hemp oil, peptides (such as glycyl-histidyl-lysine (GHK)-Cu and palmitoyl KTTKS), corticosteroids, pharmaceutically acceptable salts of any of the preceding, or any combination thereof. In an exemplary embodiment, the topical acne agent is salicylic acid or a pharmaceutically acceptable salt thereof. In an exemplary embodiment, the salicylic acid or the pharmaceutically acceptable salt thereof is present in an amount of about 0.05 to about 10 wt. % of the adhesive composition, including the more specific ranges described herein.

In an exemplary embodiment, the adhesive composition comprises a solvent, which includes but is not limited to, an alcohol (such as a polyhydric alcohol), water, or a combination thereof. In an exemplary embodiment, the polyhydric alcohol is propylene glycol, ethylene glycol, glycerol or a combination thereof. In an exemplary embodiment, the solvent is present in an amount of about 0.5 to about 25 wt. %, such as about 1 to about 15 wt. %, such as about 5 to about 15 wt. %, such as about 10 to about 25 wt. %, of the adhesive composition.

In an exemplary embodiment, the adhesive composition is positioned on an entire side of the backing. In an exemplary embodiment, the adhesive composition is positioned on only a portion of an entire side of the backing. In an exemplary embodiment, the adhesive composition is affixed or coated only on the surface of the backing. In an exemplary embodiment, the adhesive composition is partially embedded in at least a portion of the backing in a range of about 50 to 100%, such as about 60 to 100%, such as about 70 to 100%, such as about 80 to 100%, such as about 90 to 100%.

In an exemplary embodiment, the adhesive composition comprises at least one of glycerin, pectin, a skin conditioner (such as vitamin E, aloe, lanolin, calamine or any combination thereof), an antimicrobial agent (such as antifungal agent), an antiseptic agent (such as iodine, triclosan, silver, chlorhexidine, chlorhexidine salts, PHMB and/or octenidine), an antibiotic agent (such as erythromycin, tetracycline or cephalosporin), a carotenoid, an analgesic and a hemostyptic in an amount of about 0.01 to about 50 wt. %, such as about 0.1 to 50 wt. %, such as about 1 to 50 wt. %, such as about 5 to about 50 wt., such as about 10 to about 50 wt. %, such as about 20 to about 50 wt. %, of the adhesive composition.

In an exemplary embodiment, the adhesive composition has a thickness in an amount of 0.01 mm to about 1.5 mm, such as about 0.10 to about 0.60 mm, such as about 0.20 to about 0.50 mm, including other ranges described herein.

In an exemplary embodiment, more than one adhesive patch (such as 2 or 4 or 6 or 8 or 10 or 12 or 16) can be affixed to or mounted on the release liner. In an exemplary embodiment, the adhesive patch is crescent-shaped or rectangular or circular or oval.

In an exemplary embodiment, the adhesive patch or the backing has a diameter of about 0.1 to about 5 inches, such as about 0.2 to about 2 inches, such as about 0.3 to about 1 inch, such about 0.3 to about 0.5 inches, including other ranges described herein.

In an exemplary embodiment, the present invention also provides for a method for treating or preventing acne, dermatitis or warts in a mammal (e.g., a human) in need or risk thereof by applying to the targeted skin surface of the mammal an adhesive patch of the present invention for an period of time effective to treat or prevent acne, dermatitis or warts. In an exemplary embodiment, the targeted skin surface of the mammal is the face, neck, shoulder, chest, back, or any combination thereof. In an exemplary embodiment, the effective period of time is about 10 minutes to about 72 hours, including the more specific ranges described herein.

In an exemplary embodiment, the adhesive patch according to the invention is applied to the lip(s) of a mammal for preventing or treating cold sores. Application of the adhesive path to the lip(s) includes the region of the lip(s) alone or a portion of the patch can be applied to the lip (such as the edge of the lip) and the remaining portion of the patch can be applied to the surrounding skin.

The thickness of the adhesive composition layer of the patch of the present invention may be substantially constant over the surface or the adhesive composition layer or alternatively, the adhesive composition layer may have a thicker portion at the center of the composition compared to the edges of the composition layer—i.e., a beveled edge, where in various particular embodiments, the thickness of the edge is 10% or 20% or 50% or 75% of the thickness of the center.

Any suitable amount of a pressure sensitive adhesive can be present in the therapeutic adhesive composition, provided the amount of pressure sensitive adhesive effectively provides the requisite adhesiveness to the backing and/or the liner and remains stable in the therapeutic adhesive composition over a prolonged period of time. Typically, the therapeutic adhesive composition can include a pressure sensitive adhesive in an amount of about 0.01 to about 99.99 wt. % of the therapeutic adhesive composition, such as about 0.1 to about 99.9 wt. %, such as about 1 to about 99 wt. %, such as about 2 to about 98 wt. %, such as about 3 to about 97 wt. %, such as about 5 to about 95 wt. %, such as about 10 to about 90 wt. %, such as about 15 to about 85 wt. %, such as about 20 to about 80 wt. %, such as about 25 to about 75 wt. %, such as about 30 to about 70 wt. %, such as about 40 to about 60 wt. %.

As used herein, "acne" refers to an inflammatory follicular, papular, or pustular eruption involving the sebaceous glands. The types of acne include acne conglobata, chloracne, and rosacea. See, e.g., Stedman's Medical Dictionary, 25th Ed., illustrated, Williams & Wilkins, Baltimore, Md., pp. 15-16 (1990).

The adhesive patch of the present invention can be applied to any suitable skin surface of the subject in need thereof. Suitable skin surfaces in which the patch can be applied include the face, neck, shoulder, chest, elbow, inner elbow and back. In an exemplary embodiment, the adhesive patch of the present invention is applied to the face (including lips) of the subject.

The adhesive patch of the present invention also serves to cosmetically cover noticeable skin blemishes such as acne and/or pimples. Many commercial products do not effectively cover the entire skin blemish for prolonged periods of time, but the adhesive patch of the present invention can accomplish this for over 4 hours, such as over 8 hours, such as over 12 hours, such as over 24 hours, such as over 48 hours while simultaneously therapeutically treating the skin blemish.

Release Liner

The release liner in the adhesive patch arrangement of the present invention is to coat and protect the adhesive composition of the adhesive patch to prevent the surface of the adhesive composition from being contaminated before attachment. The release liner is provisionally attached to the adhesive composition in a readily detachable state, typically requiring only a peeling force to detach.

Suitable compositions of the release liners of the present invention include those that are generally known to be used with skin-friendly adhesive compositions, such as release liners produced by subjecting a surface of a plastic sheet or a film of a polyolefin (such as polyethylene or polypropylene or a laminate of a plastic film and paper) to a silicone release treatment. In an exemplary embodiment, the thickness of the release liner has a thickness of about 0.01 to about 1.0 mm, such as about 0.03 to about 0.7 mm, such as about 0.07 to about 0.5 mm, such as about 0.1 to about 0.4 mm, including other ranges described herein.

In an exemplary embodiment, the area of the release liner is larger than the area of the adhesive patch—i.e., the area of the combined backing and the adhesive composition. In the exemplary embodiment where the release liner is larger than the adhesive patch, the portion of the release liner that extends beyond the adhesive patch may be held (gripped) by using the fingers of one hand and peeled away from the therapeutic adhesive composition to detach the release liner from the therapeutic adhesive composition. In an exemplary embodiment, the release liner covering the therapeutic adhesive composition contains a perforated pattern or a slit that allows for facile separation (peeling away) of the liner (in two portions) from the therapeutic adhesive composition. In this embodiment, the adhesive patch is attached to the skin of a mammal in need thereof in a two-step process where in the first step, one of the two portions of the liner is peeled away, exposing a portion of the therapeutic adhesive composition which is then attached (affixed) to the desired area of the skin of the mammal. In the second step, the second (remaining) portion of the liner is peeled away while the adhesive patch is still attached to the subject's skin via the previously exposed portion of the therapeutic adhesive composition, thus exposing the remaining portion of the therapeutic adhesive composition, which is then attached (affixed) to the subject's skin. This tandem mode of applying the adhesive patch of the present invention allows for a rapid and substantially error-free application of the patch to the subject's skin while minimizing mishaps such as having one portion of the adhesive composition undesirably attaching to another portion of the patch. This type of mishap prevents full contact of the therapeutic adhesive composition with the skin, which reduces the therapeutic benefit of the patch and also undesirably renders the patch less conspicuous on the surface of the subject's skin due to its lack of a completely flat surface.

Slit and/or Perforation

In an exemplary embodiment, the slit that forms the slit line in a single adhesive patch of the present invention partitions the release liner into two portions, thus allowing for a tandem (two-step) application of the adhesive patch on the skin of a mammalian subject. In an exemplary embodiment, the liner is cut to a depth in the range of at least 10%, such as 15% or 20% or 30% or 40% or 50% or 60% or 70% or up to 100% of the thickness of the liner to allow ready removal of the liner from the therapeutic adhesive composition.

In addition to a straight line, the slit line may be in any shape that allows for facile separation of the liner into multiple portions. For example, the shape may be a curve, a zigzag line, an arc shape, a wave shape or a saw-tooth shape.

In an exemplary embodiment, liner is perforated to also facilitate a tandem (two-step) application of the adhesive patch on the skin of a mammalian subject. In addition to a straight line, the perforation may be in any shape that allows for facile separation of the liner into multiple portions. For example, the shape may be a curve, a zigzag line, an arc shape, a wave shape or a saw-tooth shape.

In an exemplary embodiment, the improved release liner system contains a combination of one or more perforated lines and one or more slits.

The adhesive patch arrangement of the present invention is suitable for medical applications and cosmetic applications.

EXAMPLES

The following non-limiting exemplary formulations illustrate suitable adhesive compositions for use in combination with a therapeutic agent in the therapeutic adhesive compositions of the present invention.

Example 1

(a) 5 to 20 wt % or 5 to 15 wt % or 10 to 15 wt % of an elastomer;
(b) 1 to 10 wt % or 2 to 10 wt % or 5 to 10 wt % of a mineral oil plasticizer;
(c) 20 to 60 wt % or 25 to 55 wt % or 30 to 55 wt % or 35 to 50 wt % of a tackifier; and
(d) 20 to 60 wt % or 25 to 50 wt % or 30 to 50 wt % or 30 to 45 wt % of an absorbent,
where the total weight percent of components (a) through (d) is 100%.

In exemplary embodiments of the above formulation of Example 1, the elastomer is selected from the group consisting of Kraton SEBS, Kraton SIS, Kraton SBS and mixtures thereof; the mineral oil plasticizer is selected from the group consisting of mineral oil, plant oil, hydrogenated botanical oil and mixtures thereof; the tackifier is selected from the group consisting of acrylic resin, c5 tackifier, hydrogenated hydrocarbon resin and mixtures thereof; and the absorbent is selected from the group consisting of carboxymethylcelluose, gelatin, SAP super absorbents and mixtures thereof. The therapeutic agent is one or more of benzoyl peroxide, salicylic acid, glycolic acid and sulfur.

Example 2

(a) 10 to 15 wt % of mineral oil;
(b) 25 to 50 wt % or 30 to 40 wt % of carboxymethylcellulose;
(c) 3 to 15 wt % or 5 to 10 wt % of KRATON° 1161; and
(d) 25 to 45 wt % or 30 to 40 wt % of ARKON° P115,
where the total weight percent of components (a) through (d) is 100%.

Example 3

(a) 3 to 10 wt % or 5 to 10 wt % of mineral oil;
(b) 25 to 50 wt % or 30 to 40 wt % of carboxymethylcellulose;
(c) 10 to 25 wt % or 15 to 20 wt % of KRATON° 1161; and
(d) 25 to 55 wt % or 35 to 45 wt % of FORAL° 85,
where the total weight percent of components (a) through (d) is 100%.

Example 4

(a) 35 to 65 wt % or 45 to 55 wt % of mineral oil; and
(b) 35 to 65 wt % or 45 to 55 wt % of carboxymethylcellulose,
where the total weight percent of components (a) and (b) is 100%.

Example 5

(a) 20 to 45 wt % or 30 to 40 wt % of alpha linolenic acid;
(b) 15 to 40 wt % or 20 to 35 wt % of carboxymethylcellulose;
(c) 20 to 45 wt % or 25 to 40 wt % of KRATON®; and
(d) 10 to 25 wt % or 15 to 20 wt % of FORAL° 85,
where the total weight percent of components (a) through (d) is 100%.

Example 6

(a) 1 to 15 wt % or 5 to 10 wt % of myristic acid;
(b) 20 to 50 wt % or 30 to 40 wt % of carboxymethylcellulose;
(c) 10 to 30 wt % or 15 to 25 wt % of KRATON®; and
(d) 20 to 55 wt % or 35 to 50 wt % of FORAL° 85,
where the total weight percent of components (a) through (d) is 100%.

Example 7

(a) 20 to 45 wt % or 25 to 40 wt % of a 1:1:1 mixture of mineral oil and alpha linolenic acid and myristic acid;
(b) 10 to 35 wt % or 15 to 30 wt % of carboxymethylcellulose;
(c) 15 to 40 wt % or 25 to 40 wt % of KRATON®; and
(d) 10 to 30 wt % or 15 to 25 wt % of FORAL° 85,
where the total weight percent of components (a) through (d) is 100%.

Example 8

(a) 35 to 65 wt % or 40 to 55 wt % of a 1:2:1 mixture of mineral oil and alpha linolenic and myristic acid;
(b) 15 to 40 wt % or 20 to 35 wt % of carboxymethylcellulose;
(c) 5 to 30 wt % or 5 to 20 wt % of KRATON®; and
(d) 1 to 20 wt % or 10 to 15 wt % of FORAL° 85,
where the total weight percent of components (a) through (d) is 100%.

All patents and other publications cited herein are incorporated by reference in their entireties.

The invention claimed is:

1. A flexible adhesive patch arrangement comprising in the following order:
   a flexible adhesive patch comprising:
      a backing having two sides, wherein the backing is continuous without perforations or indentations; and
      a therapeutic adhesive composition coated on at least a portion of one side of the backing, wherein the therapeutic adhesive composition is capable of adhering to mammalian skin; and
   a liner completely covering the therapeutic adhesive composition, wherein the liner contains a means for readily separating the liner into two portions, with each portion being in contact with the therapeutic adhesive composition;
   wherein an area of the liner is larger than an area of the adhesive composition;
   wherein each of the backing and the therapeutic adhesive composition has a circular or oval shape; and
   wherein the backing has a diameter of 0.2 inches to 0.5 inches.

2. The adhesive patch arrangement according to claim 1, wherein the means for separating is a perforated pattern or a slit that partially or completely penetrates the liner.

3. The adhesive patch arrangement according to claim 1, wherein the liner comprises one or more of a polyester film, a polyolefin film, siliconized paper or a plastic laminated paper.

4. The adhesive patch arrangement according to claim 1, wherein the liner has a thickness of about 0.01 to about 0.5 mm.

5. The adhesive patch arrangement according to claim 1, wherein the backing has a thickness of about 0.02 mm to about 1.0 mm.

6. The adhesive patch arrangement according to claim 1, wherein the backing comprises polycellulose fibers, polyester fibers, polyurethane fibers, polyolefin fibers, polyamide fibers, cotton fibers, copolyester fibers, a polycellulose film, a polyurethane film, a polyester film, a polyethylene film, a polyolefin film or any mixture thereof.

7. The adhesive patch arrangement according to claim 1, wherein the therapeutic adhesive composition comprises one or more of a polyacrylamide, xanthum gum, guar gum, a hydrocolloid, a starch, a vinyl acetate copolymer, polyvinyl pyrrolidone, polyvinyl alcohol, polyethylene oxide, a polyacrylate, polymaleic acid, polymaleic anhydride, a polyurethane, a polyurea, maltodextrin, carboxymethyl cellulose, carboxypropyl cellulose, a hydrocolloid, a hydrogel, an acrylic, a polyurethane, a rubber or a silicone gel.

8. The adhesive patch arrangement according to claim 1, wherein the therapeutic adhesive composition has a thickness of about 0.01 mm to about 1.5 mm.

9. The adhesive patch arrangement according to claim 1, wherein the therapeutic adhesive composition comprises a topical acne agent.

10. The adhesive patch arrangement according to claim 1, wherein the therapeutic adhesive composition has a center and edges, and wherein the therapeutic adhesive composition is thicker at the center than at the edges.

11. The adhesive patch arrangement according to claim 1, wherein edges of the backing contact the liner to enclose the therapeutic adhesive composition between the backing and the liner.

12. A flexible adhesive patch arrangement comprising in the following order:
 a flexible adhesive patch comprising:
  a backing having two sides, wherein the backing is a single continuous layer without perforations or indentations; and
  a therapeutic adhesive composition coated on at least a portion of one side of the backing, wherein the therapeutic adhesive composition is capable of adhering to mammalian skin; and
 a liner completely covering the therapeutic adhesive composition, wherein the liner includes a perforated pattern or a slit that partially or completely penetrates the liner for separating the liner into two portions, with each portion being in contact with the therapeutic adhesive composition;
 wherein the backing has a thickness of about 0.03 mm to about 0.8 mm.

13. A sheet composed of multiple copies of the adhesive patch arrangement according to claim 2 arranged in parallel, wherein the slit or the perforated pattern present in each copy forms a single uninterrupted line that extends the length or width of the sheet.

14. The sheet according to claim 13, wherein each copy is separated from an adjacent copy by a different readily separable perforated pattern or slit, and wherein each different perforated pattern or slit cumulatively forms a single uninterrupted line that extends the length or width of the sheet.

15. A method for attaching the flexible adhesive patch arrangement of claim 1 to a targeted skin area of a mammal in need thereof, the method comprising:
 detaching one of the two liner portions from the flexible adhesive patch arrangement to expose a first portion of the therapeutic adhesive composition of the flexible adhesive patch;
 attaching the exposed first portion of the therapeutic adhesive composition to the targeted skin area;
 detaching the second of the two liner portions from the flexible adhesive patch arrangement to expose a remaining portion of the therapeutic adhesive composition of the flexible adhesive patch while the exposed first portion of the therapeutic adhesive composition remains attached to the targeted skin area; and
 attaching the exposed remaining portion of the therapeutic adhesive composition to complete attachment of the flexible adhesive patch to the targeted skin area.

16. The method according to claim 15, wherein the means for readily separating the liner is a perforated pattern or a slit that partially or completely penetrates the liner.

17. A method for treating or preventing a disorder or condition of the skin of a mammal in need thereof, comprising applying to an affected surface of the skin of the mammal the adhesive patch arrangement according to claim 1 for an period of time effective to treat or prevent the skin disorder or condition.

18. The method according to claim 17, wherein the disorder or condition is selected from the group consisting of acne, warts, *Herpes labialis* (cold sores), atopic dermatitis, seborrheic dermatitis, contact dermatitis, allergic contact eczema, insect bites, lentigo and wrinkles.

* * * * *